United States Patent
Arvisais et al.

(10) Patent No.: US 12,354,719 B2
(45) Date of Patent: Jul. 8, 2025

(54) TOUCHLESS REGISTRATION USING A REFERENCE FRAME ADAPTER

(71) Applicant: Medtronic Navigation, Inc., Louisville, CO (US)

(72) Inventors: Morgan Suzanne Arvisais, Longmont, CO (US); Samantha Joanne Preston, Denver, CO (US)

(73) Assignee: Medtronic Navigation, Inc., Lafayette, CO (US)

( * ) Notice: Subject to any disclaimer, the term of this patent is extended or adjusted under 35 U.S.C. 154(b) by 308 days.

(21) Appl. No.: 18/077,013

(22) Filed: Dec. 7, 2022

(65) Prior Publication Data

US 2024/0194306 A1    Jun. 13, 2024

(51) Int. Cl.
*G16H 10/60*    (2018.01)
*A61B 34/20*    (2016.01)
*A61B 90/00*    (2016.01)

(52) U.S. Cl.
CPC ............. *G16H 10/60* (2018.01); *A61B 34/20* (2016.02); *A61B 90/361* (2016.02); *A61B 2034/2051* (2016.02)

(58) Field of Classification Search
CPC ...... G16H 10/60; A61B 34/20; A61B 90/361; A61B 2034/2051
See application file for complete search history.

(56) References Cited

U.S. PATENT DOCUMENTS

| | | | | |
|---|---|---|---|---|
| 10,993,771 | B2 * | 5/2021 | Srimohanarajah | A61B 46/00 |
| 2008/0112604 | A1 * | 5/2008 | Lloyd | A61B 6/547 |
| | | | | 382/131 |
| 2008/0119712 | A1 * | 5/2008 | Lloyd | A61B 90/36 |
| | | | | 600/407 |
| 2012/0046542 | A1 * | 2/2012 | Csavoy | A61B 34/20 |
| | | | | 600/424 |
| 2016/0278875 | A1 * | 9/2016 | Crawford | A61B 90/98 |
| 2016/0324583 | A1 * | 11/2016 | Kheradpir | A61B 46/10 |
| 2016/0354009 | A1 * | 12/2016 | Schroeder | A61B 5/062 |
| 2017/0239015 | A1 * | 8/2017 | Sela | A61B 46/10 |

(Continued)

FOREIGN PATENT DOCUMENTS

| | | | | |
|---|---|---|---|---|
| EP | 3868325 | | 8/2021 | |
| WO | WO-2016058088 | A1 * | 4/2016 | A61B 34/20 |

OTHER PUBLICATIONS

O. V. Olesen, S. H. Keller, M. Sibomana, R. Larsen, B. Roed and L. Højgaard, "Automatic thresholding for frame-repositioning using external tracking in PET brain imaging," IEEE Nuclear Science Symposium & Medical Imaging Conf, Knoxville, TN, USA, 2010, pp. 2669-2675, doi: 10.1109/NSSMIC.2010.5874275 (Year: 2010).*

(Continued)

*Primary Examiner* — Sun M Li
(74) *Attorney, Agent, or Firm* — Sheridan Ross P.C.

(57) ABSTRACT

Systems and methods for touchless registration using a reference frame adapter is provided. A first image of a region of a patient and a second image of the region of the patient and a reference frame adapter may be received. The reference frame adapter may be configured to selectively attach to a patient reference frame positioned near the region of the patient. The second image may be registered to the first image based on the reference frame adapter.

20 Claims, 9 Drawing Sheets

(56) References Cited

U.S. PATENT DOCUMENTS

2018/0193097 A1* 7/2018 McLachlin ............ A61B 34/20
2018/0368918 A1* 12/2018 Tatsui .................... A61B 34/20
2022/0309690 A1* 9/2022 Paitel ...................... G06T 17/20
2023/0074362 A1* 3/2023 Datteri ................. G06V 40/165

OTHER PUBLICATIONS

R. Hussain, A. Lalande, C. Guigou and A. Bozorg-Grayeli, "Contribution of Augmented Reality to Minimally Invasive Computer-Assisted Cranial Base Surgery," in IEEE Journal of Biomedical and Health Informatics, vol. 24, No. 7, pp. 2093-2106, Jul. 2020, doi: 10.1109/JBHI.2019.2954003. k (Year: 2020).*

C. Faria, W. Erlhagen, M. Rito, E. De Momi, G. Ferrigno and E. Bicho, "Review of Robotic Technology for Stereotactic Neurosurgery," in IEEE Reviews in Biomedical Engineering, vol. 8, pp. 125-137, 2015, doi: 10.1109/RBME.2015.2428305. (Year: 2015).*

A. H. Brandt et al., "Clinical evaluation of Synthetic Aperture Sequential Beamforming and Tissue Harmonic Imaging," 2014 IEEE International Ultrasonics Symposium, Chicago, IL, USA, 2014, pp. 1312-1315, doi: 10.1109/ULTSYM.2014.0324. (Year: 2014).*

International Search Report and Written Opinion for International (PCT) Patent Application No. PCT/IB2023/062192, dated Feb. 23, 2024, 14 pages.

* cited by examiner

TOUCHLESS REGISTRATION USING A REFERENCE FRAME ADAPTER

BACKGROUND

The present disclosure is generally directed to registration, and relates more particularly to touchless registration using a reference frame adapter.

A registration process may be carried out to correlate preoperative images with intraoperative images. Imaging may be used as part of the registration process. The registration may be used to enable navigation and/or to enable a robotic system to assist a surgeon or to autonomously perform a surgical procedure.

BRIEF SUMMARY

Example aspects of the present disclosure include:

A system for contactless registration according to at least one embodiment of the present disclosure comprises a processor; and a memory storing data for processing by the processor, the data, when processed, causes the processor to: receive a first image of a region of a patient; receive a second image of the region of the patient and a reference frame adapter, the reference frame adapter configured to selectively attach to a patient reference frame positioned near the region of the patient; and register the second image to the first image based on the reference frame adapter.

Any of the aspects herein, wherein the reference frame adapter includes at least one reference marker disposed on a surface of the reference frame adapter.

Any of the aspects herein, wherein the patient reference frame includes at least one reference marker disposed on a surface of the patient reference frame.

Any of the aspects herein, wherein the reference frame adapter is configured to selectively attach to the reference frame via at least one of a clamp, adhesive, a magnetic attachment, a snap fit, a clip-on fit, a screw attachment, a pin attachment, and a spring attachment.

Any of the aspects herein, wherein the reference frame adapter covers at least a portion of the reference frame.

Any of the aspects herein, wherein the second image comprises a 3D scan and the region of the patient comprises a face of the patient.

Any of the aspects herein, further comprising a navigation system configured to track the patient reference frame, wherein the memory stores further data for processing by the processor that, when processed, causes the processor to: correlate a pose of the reference frame adapter with a pose of the reference frame; and track the patient reference frame.

Any of the aspects herein, wherein the reference frame adapter is removed from the patient reference frame after the second image is registered to the first image.

A system for contactless registration according to at least one embodiment of the present disclosure comprises a processor; and a memory storing data for processing by the processor, the data, when processed, causes the processor to: receive a first image of a region of a patient; receive a second image of the region of the patient and an electromagnetic (EM) reference frame adapter, the EM reference frame adapter configured to selectively attach to a patient EM tracker positioned near the region of the patient; and register the second image to the first image based on the reference frame adapter.

Any of the aspects herein, wherein the EM reference frame adapter includes at least one reference marker disposed on a surface of the reference frame adapter.

Any of the aspects herein, wherein the reference frame adapter is configured to selectively attach to the EM tracker.

Any of the aspects herein, wherein the second image comprises a 3D scan and the region of the patient comprises a face of the patient.

Any of the aspects herein, further comprising a navigation system configured to track the EM tracker, wherein the memory stores further data for processing by the processor that, when processed, causes the processor to: correlate a pose of the EM reference frame adapter with a pose of the EM tracker; and track the EM tracker.

Any of the aspects herein, wherein the EM reference frame adapter is removed from the EM tracker after the second image is registered to the first image.

A system for contactless registration according to at least one embodiment of the present disclosure comprises a navigation system configured to track a patient reference frame; a processor; and a memory storing data for processing by the processor, the data, when processed, causes the processor to: receive a first image of a region of a patient; receive a second image of the region of the patient and a reference frame adapter, the reference frame adapter configured to selectively attach to a patient reference frame positioned near the region of the patient; register the second image to the first image based on the reference frame adapter; and cause the navigation system to track the patient reference frame.

Any of the aspects herein, wherein the reference frame adapter includes at least one reference marker disposed on a surface of the reference frame adapter.

Any of the aspects herein, wherein the patient reference frame includes at least one reference marker disposed on a surface of the patient reference frame.

Any of the aspects herein, wherein the reference frame adapter is configured to selectively attach to the reference frame via at least one of a snap fit, a clip-on fit, a screw attachment, a pin attachment, and a spring attachment.

Any of the aspects herein, wherein the reference frame adapter covers at least a portion of the reference frame.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
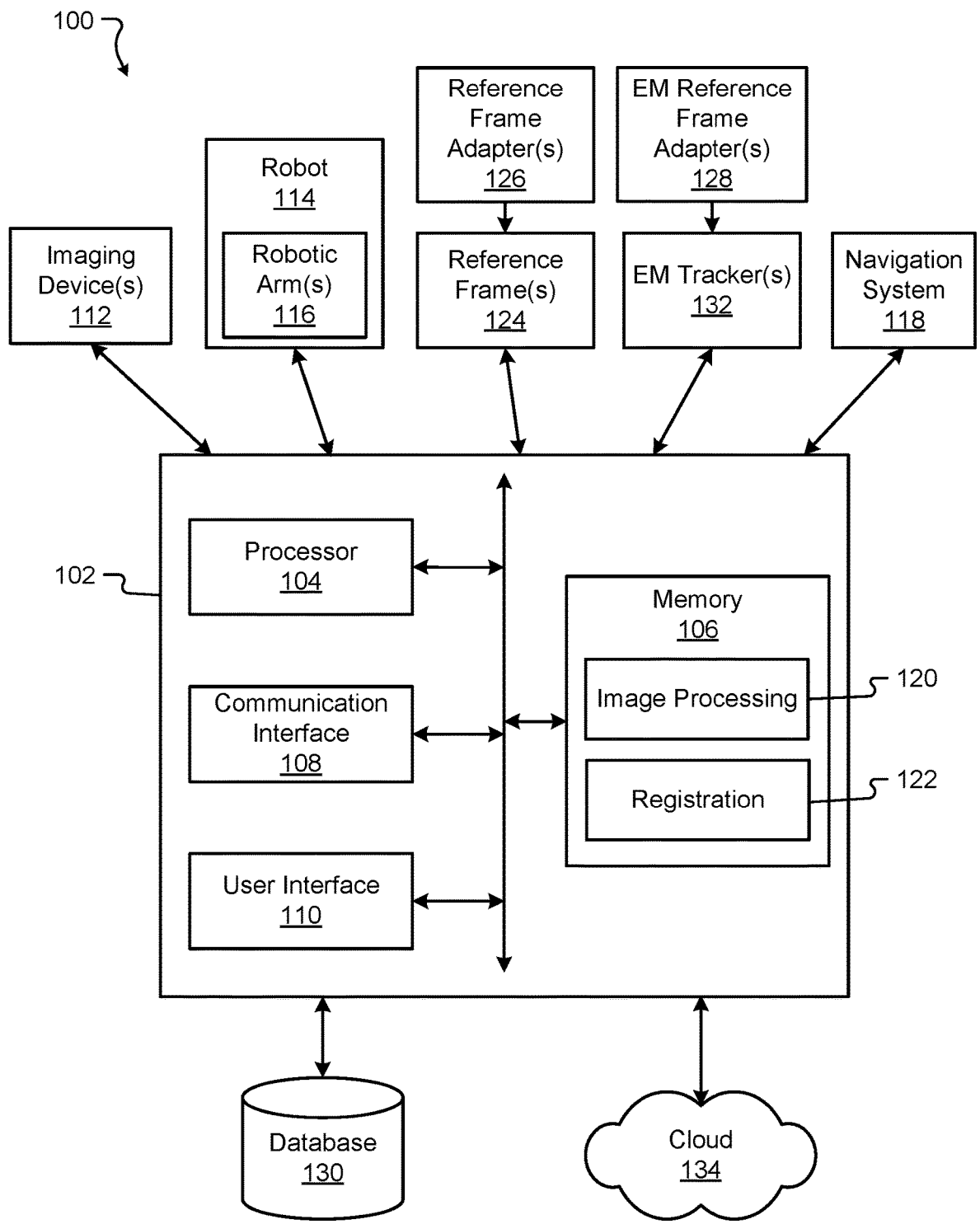
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10× Fusion processors; Apple A11, A12, A12X, A12Z, or A13 Bionic processors; or any other general purpose microprocessors), graphics processing units (e.g., Nvidia Geforce RTX 2000-series processors, Nvidia Geforce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Contactless registration for navigation of one or more regions of a patient such as, for example, cranial and/or ears, nose, and throat (ENT) is conventionally a process that uses three-dimensional (3D) scanner(s) to capture data of the region(s) of the patient (such as the patient's head) and a patient reference frame. Data from the 3D scanners is used to register the patient's 3D scan to one or more pre-operative images. Conventional patient reference frames may not be easily recognizable by the 3D scanners due to the shape, material, geometry, and/or the like of the patient reference frames, which may interfere with the contactless registration using the 3D scanners.

According to at least one embodiment of the present disclosure, a reference frame adapter is provided that is configured to affix to any existing patient reference frame in one or more orientations so as to provide a unique object that is recognizable by the 3D scanners. Such reference frame adapter will enable any patient reference frame to be registered in 3D space by the 3D scanners. Thus, the reference frame adapter can be attached to the patient reference frame to enable an initial registration and/or full registration, and then removed from the patient reference frame such that the patient reference frame can be used for a remaining portion of the registration and/or during navigation.

Embodiments of the present disclosure provide technical solutions to one or more of the problems of (1) enabling use of existing patient reference frames for touchless registration, (2), enabling detection of existing patient reference frames by 3D scanner(s), and (3) decreasing surgical procedure time.

Turning first to FIG. 1, a block diagram of a system 100 according to at least one embodiment of the present disclosure is shown. The system 100 may be used to perform contactless registration and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134. It will be appreciated that in some embodiments, the navigation system 118 includes the computing device 102 (e.g., the computing device 102 is integrated with the navigation system 118 or is a component of the navigation system 118).

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the method 600 described herein, or of any other methods. The memory 106 may store, for example, instructions and/or machine learning models that support one or more functions of the navigation system 118 and/or the robot 114. For instance, the memory 106 may store content (e.g., instructions and/or machine learning models) that, when executed by the processor 104, enable image processing 120 and/or registration 122. Such content, if provided as in instruction, may, in some embodiments, be organized into one or more applications, modules, packages, layers, or engines.

The image processing 120 enables the processor 104 to process image data of an image (received from, for example, the imaging device 112, an imaging device of the navigation system 118, or any imaging device) for the purpose of, for example, identifying information about one or more anatomical elements or objects such as a reference frame adapter 126, an EM reference frame adapter 128, and/or one or more reference markers disposed on a reference frame 124, the reference frame adapter 126, and/or the EM reference frame adapter 128 depicted in the image. The information may comprise, for example, a pose of the markers, the reference frame adapter 126, or the EM reference frame adapter 128, a pattern defined by the markers, a QR code, or a barcode.

The registration 122 enables the processor 104 to correlate an image with another image. The registration 122 may enable the processor 104 to also correlate identified anatomical elements and/or individual objects in one image with identified anatomical elements and/or individual objects in another image. The registration 122 may enable information about the anatomical elements and the individual objects (such as, for example, the reference frame adapter 126, the EM reference frame adapter 128, and/or reference marker(s)) to be obtained and measured. For example, a pose of the reference frame adapter 126 or the EM reference frame adapter 128 may be obtained.

Alternatively or additionally, the memory 106 may store other types of content or data (e.g., machine learning models, artificial neural networks, deep neural networks, etc.)

that can be processed by the processor 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image or scan anatomical feature(s) (e.g., a patient's face, bone, veins, tissue, etc.), other aspects of patient anatomy, and/or objects such as the reference frame adapter 126, the EM reference frame adapter 128, reference markers, and/or the reference frame 124 to yield image data (e.g., image data depicting or corresponding to a bone, veins, tissue, etc. and/or the objects). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. For example, the imaging device 112 may comprise a scanner configured to scan a region of the patient (e.g., a patient's head, face, etc.) and yield a 3D image of the region of the patient. The scanner may also be configured to scan the region of the patient and a reference frame adapter such at the reference frame adapter 126 or an EM reference frame adapter such as the EM reference frame adapter 128. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms 116 may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (e.g., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The reference markers may also be supported on a reference frame 124. In some embodiments, the reference frame 124 may be placed on or near a patient. As previously described, in some instances where the imaging device 112 comprises a 3D scanner, the reference frame 124 may be difficult to detect when performing an initial 3D scan of a region (during, for example, a touchless registration) of the patient and the reference frame using the 3D scanner. In such instances, a reference frame adapter 126 may be selectively attached or coupled to the reference frame 124. The reference frame adapter 126 may be more easily tracked by the 3D scanner due to the reference frame adapter's 126 geometry, material, shape, configuration, or any combination thereof. Thus, the reference frame adapter 126 enables the use of the reference frame 124 during an initial scan using the 3D scanner. When registration is complete, the reference frame adapter 126 may be removed and the reference frame 124 may be tracked by the navigation system 118. Similarly, in embodiments where the navigation system 118 uses electromagnetic (EM) tracking, an EM reference frame adapter 128 may be releasably attached to an EM tracker 132 such that the EM reference frame adapter 128 may be detected during the registration. Example embodiments of the reference frame adapter 126, the EM reference frame adapter 128, and the reference frame 124 are described in FIGS. 2A-5.

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. In some embodiments, the navigation system 118 may include the computing device 102. In other embodiments, the navigation system 118 may not include the computing device 102 and may include a processor other than the processor 104, a memory other than the memory 106, a communication interface other than the communication interface, and/or a user interface other than the user interface 110. It will be appreciate that in some embodiments, the navigation system 118, whether using a processor of the navigation system 118 or the processor 104, may execute the image processing 120 and/or the registration 122.

The navigation system 118 may include one or more cameras or other sensor(s) for tracking one or more reference markers, navigated trackers, or other objects (which may be disposed on, for example, the reference frame 124, the reference frame adapter 126, and/or the EM reference frame adapter 128) within the operating room or other room in which some or all of the system 100 is located. The one or more cameras may be optical cameras, infrared cameras, or other cameras. In some embodiments, the navigation system 118 may comprise one or more EM sensors. In various embodiments, the navigation system 118 may be used to track a position and orientation (e.g., a pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102 (in embodiments where the computing device 102 is separate from the navigation system 118), imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The database 130 may store information that correlates one coordinate system to another (e.g., one or more robotic coordinate systems to a patient coordinate system and/or to a navigation coordinate system). The database 130 may additionally or alternatively store, for example, one or more surgical plans (including, for example, pose information about a target and/or image information about a patient's anatomy at and/or proximate the surgical site, for use by the robot 114, the navigation system 118, and/or a user of the computing device 102 or of the system 100); one or more images useful in connection with a surgery to be completed by or with the assistance of one or more other components of the system 100; and/or any other useful information. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The system 100 or similar systems may be used, for example, to carry out one or more aspects of any of the methods 600 described herein. The system 100 or similar systems may also be used for other purposes.

Figure 2A:
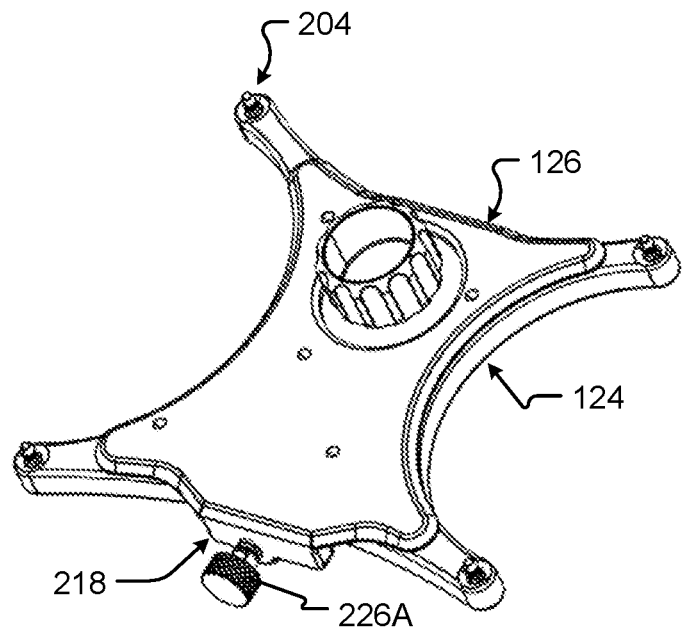
FIG. 2A is a tilted view of a reference frame adapter and a reference frame according to at least one embodiment of the present disclosure.
Figure 2B:
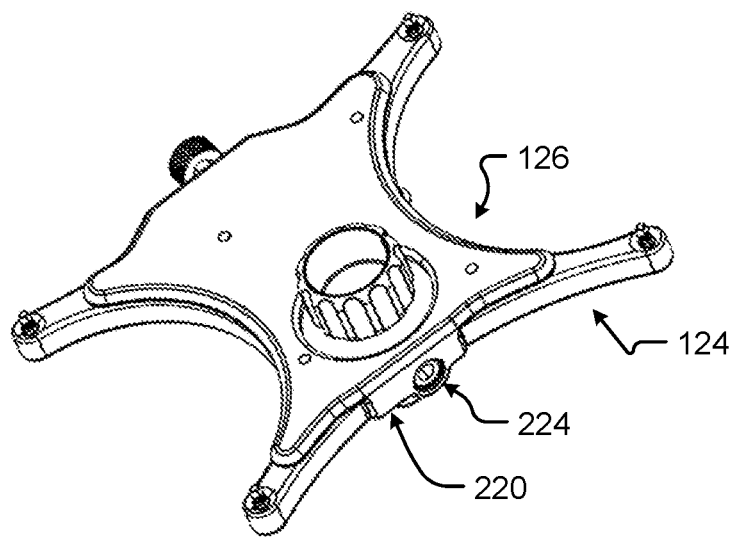
FIG. 2B is a tilted view of the reference frame adapter and the reference frame of FIG. 2A according to at least one embodiment of the present disclosure.
Figure 2C:
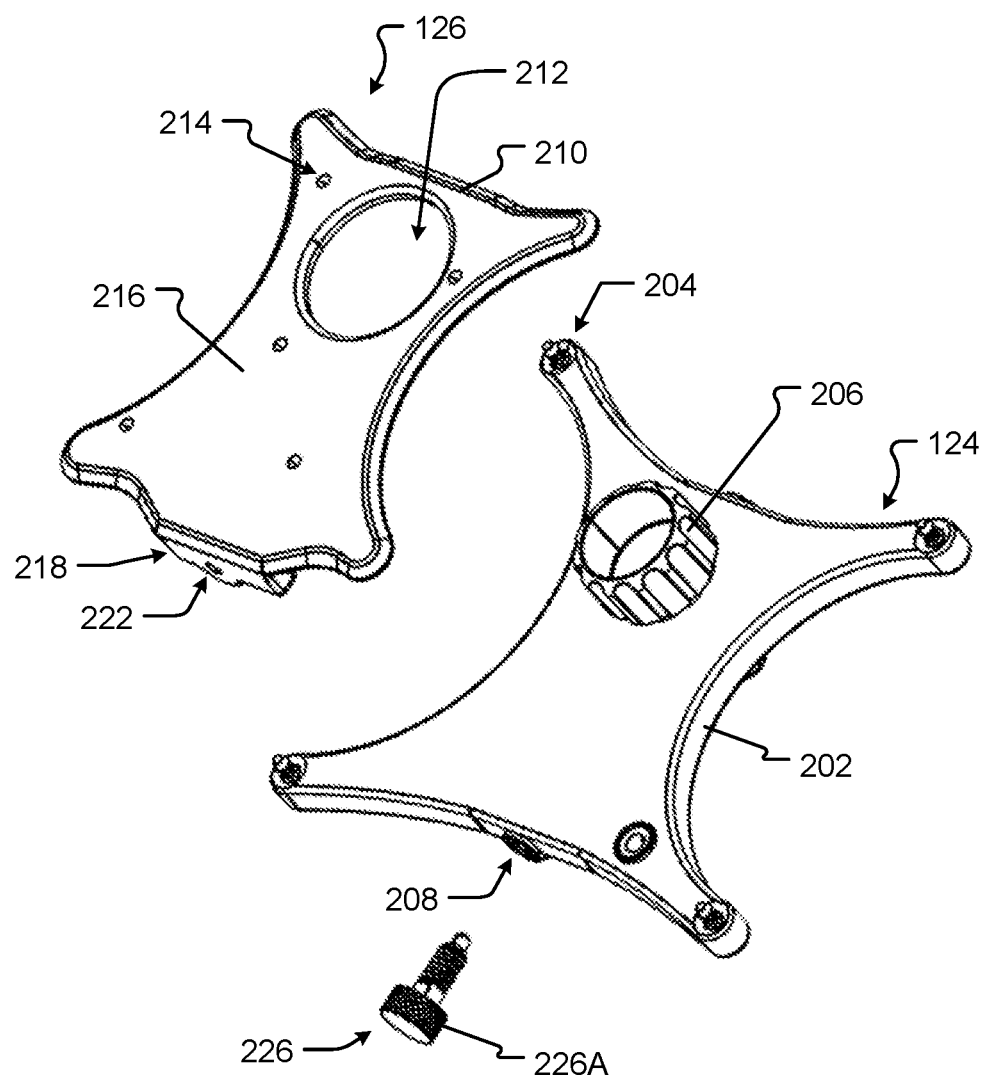
FIG. 2C is an exploded view of the reference frame adapter and the reference frame of FIG. 2A according to at least one embodiment of the present disclosure.

Turning to FIGS. 2A-2C, a tilted view, another tilted view, and an exploded view of the reference frame 124 and an embodiment of the reference frame adapter 126 according to at least one embodiment of the present disclosure are respectively shown. As previously described, the reference frame 124 may comprise a frame 202 to support one or more reference markers (not shown). The reference frame 124 includes one or more receivers 204 to receive the reference markers. In the illustrated embodiment, the receivers 204 are threaded so that a reference marker may be twisted or screwed onto (or twisted off) the reference frame 124. However, it will be appreciated that the reference frame marker may be coupled to the reference frame 124 by, for example, adhesion, bolting, riveting, press fitting, or the like. The reference markers may comprise one or more active markers, one or more passive markers, or a combination of active and passive markers. The reference markers may be, for example, light emitting diodes, infrared light emitting diodes, reflective markers, or the like. In some embodiments, the reference frame 124 may not have the one or more reference markers or the one or more reference markers may be removable. In the illustrated embodiment, the reference frame 124 also comprises a protrusion 206 extending from the frame 202 and a reference frame aperture 208. The reference frame aperture 208 may be threaded or may be unthreaded. In embodiments where the reference frame aperture 208 is threaded, the reference frame aperture 208 may receive, for example, a screw, a bolt, a threaded pin, or any other threaded projection sized to be received by the reference frame aperture 208, as will be described in more detail below. In other embodiments, the reference frame 124 may not include the protrusion 206 and/or the reference frame aperture 208.

The reference frame adapter 126 comprises a body 210 configured to selectively attach to the reference frame 124. In other words, the reference frame adapter 126 can be repeatedly attached and detached from the reference frame 124. This enables the reference frame adapter 126 to be used multiple times whether during the same surgical procedure or over the course of multiple surgical procedures. The reference frame adapter 126 covers at least 75% of the reference frame 124 in some embodiments. It will be appreciated that in other embodiments the reference frame adapter 126 may cover less than 75% of the reference frame 124.

In the illustrated embodiment, the reference frame adapter 126 comprises an opening 212 in the body 210 to receive the protrusion 206 of the reference frame 124 (in embodiments where the reference frame 124 comprises the protrusion 206). In other embodiments, the reference frame adapter 126 may not include the opening 212. The reference frame adapter 126 may also comprise one or more reference features 214 on a surface 216 of the reference frame adapter 126. The one or more reference features 214 may comprise, for example, divots, bumps, protrusions of any shape, and/or cavities of any shape. The one or more reference features 214 in some embodiments may also be configured to receive one or more reference markers. For example, the one or more reference features 214 may comprise screws or protrusions onto which a conventional reference marker can be attached thereto. The one or more reference features 214 along with, for example, a shape, geometry, and/or material of the reference frame adapter 126 enables the reference frame adapter 126 to be detected by an imaging device such as the imaging device 112, and in particular, an imaging device comprising a 3D scanner. Thus, during, for example, a registration process that uses a 3D scanner, the 3D scanner can detect a pose of the reference frame adapter 126 and the detected pose of the reference frame adapter 126 can be used to register the reference frame 124. When the registration process is completed, the reference frame adapter 126 may be removed from the reference frame 124 and the navigation system 118 may track the reference frame 124.

The reference frame adapter 126 may include, but is not limited to, a first side wall 218 (visible in FIGS. 2A and 2C) and a second side wall 220 (visible in FIG. 2B) that each extends from the body 210. It will be appreciated that in some embodiments the reference frame adapter 126 may include one side wall or more than two side walls. In still other embodiments, the reference frame adapter 126 may comprise a side wall that extends around a majority of the body 210 so as to substantially encase a side of the reference frame 202 with the side wall. The first side wall 218 and the second side wall 220 may enable a snap fit of the reference frame adapter 126 to the reference frame 124. In other embodiments, the first side wall 218 and the second side wall 220 may aid in placing and/or securing the reference frame adapter 126 onto the reference frame 124.

Figure 3A:
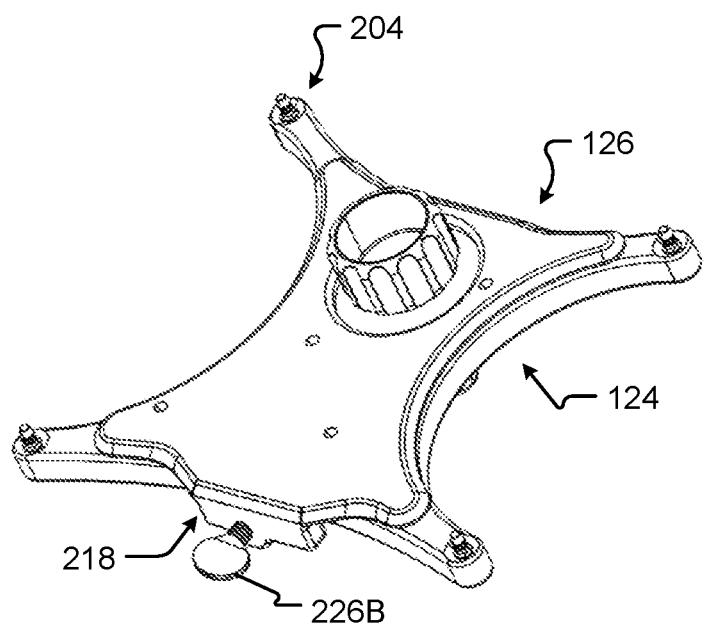
FIG. 3A is a tilted view of a reference frame adapter and a reference frame according to at least one embodiment of the present disclosure.
Figure 3B:
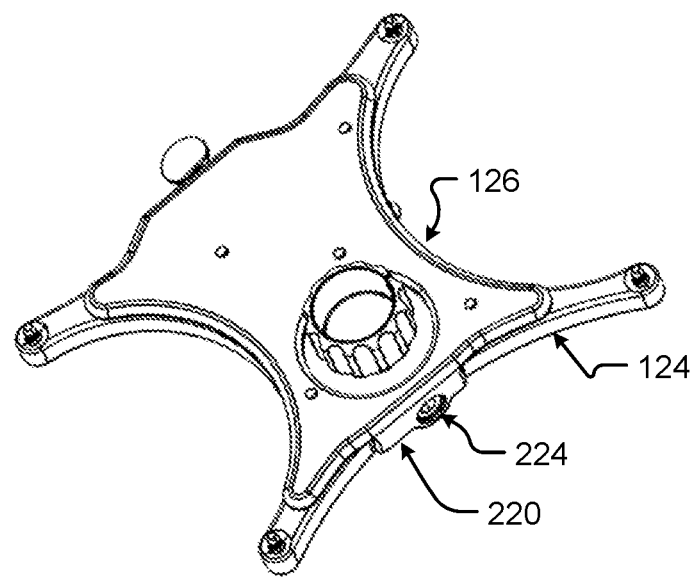
FIG. 3B is a tilted view of the reference frame adapter and the reference frame of FIG. 3A according to at least one embodiment of the present disclosure.
Figure 3C:
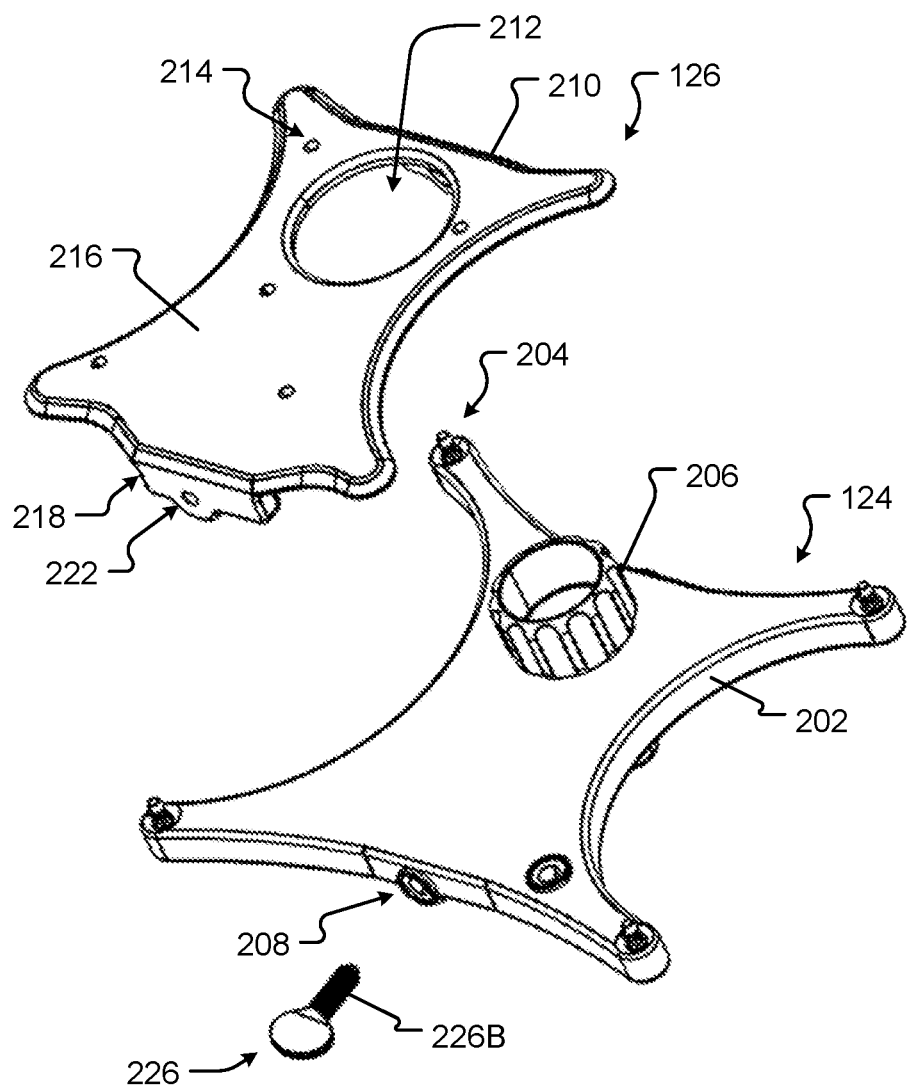
FIG. 3C is an exploded view of the reference frame adapter and the reference frame of FIG. 3A according to at least one embodiment of the present disclosure.

Each of the first side wall 218 and the second side wall 220 comprise a first aperture 222 and a second aperture 224, respectively, though in other instances only one of the first side wall 218 or the second side wall 220 may comprise an aperture. In still other embodiments, both of the first side wall 218 and the second side wall 220 may not include an aperture. The first aperture 222 and/or the second aperture 224 may be threaded although, in other embodiments, the first aperture 222 and/or the second aperture 224 may not be threaded. Whether the first aperture 222 and/or the second aperture 224 are threaded or unthreaded, the first aperture 222 and/or the second aperture 224 are configured to receive a pin 226 therethrough. In the illustrated embodiment, the pin 226 is configured to pass through the first aperture 222 and is received by the reference frame aperture 208. The reference frame aperture 208 may also be threaded or unthreaded. In embodiments where the reference frame aperture 208 is threaded, the pin 226 may also be threaded (as shown in FIGS. 3A-3C). In embodiments where the reference frame aperture 208 is unthreaded, the pin 226 may be received by the reference frame aperture 208 by, for example, press fit or the pin may be adhered to the reference frame aperture 208. In any embodiment, the pin 226 is passed through the first aperture 222 and received by the reference frame aperture 208 thereby securing the reference frame adapter 126 to the reference frame 124.

In the illustrated embodiment, the reference frame aperture 208 is unthreaded and may receive a pin 226A. The pin 226A may be partially threaded and received by the first aperture 222. In other embodiments, the pin 226A may be integrated with the first side wall 218. The pin 226A is movable between a closed position and an open position and is biased (whether by a spring or otherwise) in the closed position. The pin 226A is positioned closer towards the second side wall 220 when in the closed position and further away from the second side wall 220 when in the open position. Thus, when the reference frame adapter 126 is positioned over the reference frame 124 and the pin 226A is aligned with the reference frame aperture 208, the pin 226A is biased into the closed position and into the reference frame aperture 208, thereby securing the reference frame adapter 126 to the reference frame 124. To remove the reference frame adapter 126, the pin 226A is moved to the open position by receiving a force (from, for example, a user) to pull the pin 226A away from the first side wall 218 and into the open position such that the pin 226A is not received by the reference frame aperture 208. The reference frame adapter 126 can then be removed from the reference frame 124 when the pin 226A is in the open position.

Turning to FIGS. 3A-3C, a tilted view, another tilted view, and an exploded view of the reference frame 124 and another embodiment of the reference frame adapter 126 according to at least one embodiment of the present disclosure are respectively shown. The reference frame adapter 126 is the same as or similar to the reference frame adapter 126, except that the reference frame adapter 126 includes a pin 226B that is threaded. More specifically, and as previously described, the reference frame adapter 126 includes the first side wall 218 (visible in FIGS. 3A and 3C) and the second side wall 220 (visible in FIG. 3B) that extend from the body 210. Each of the first side wall 218 and the second side wall 220 comprise the first aperture 222 and the second aperture 224, respectively, though in other instances only one of the first side wall 218 or the second side wall 220 may comprise an aperture. The first aperture 222 and/or the second aperture 224 may be threaded although, in other embodiments, the first aperture 222 and/or the second aperture 224 may not be threaded. In the illustrated embodiment, the pin 226B is configured to pass through the first aperture 222 and is received by the reference frame aperture 208. In the illustrated embodiment, the reference frame aperture 208 is threaded and the pin 226B is also threaded. Thus, the pin 226B is received through the first aperture 222 (which may be threaded or unthreaded) and is threaded into the reference frame aperture 208 thereby securing the reference frame adapter 126 to the reference frame 124.

Figure 4A:
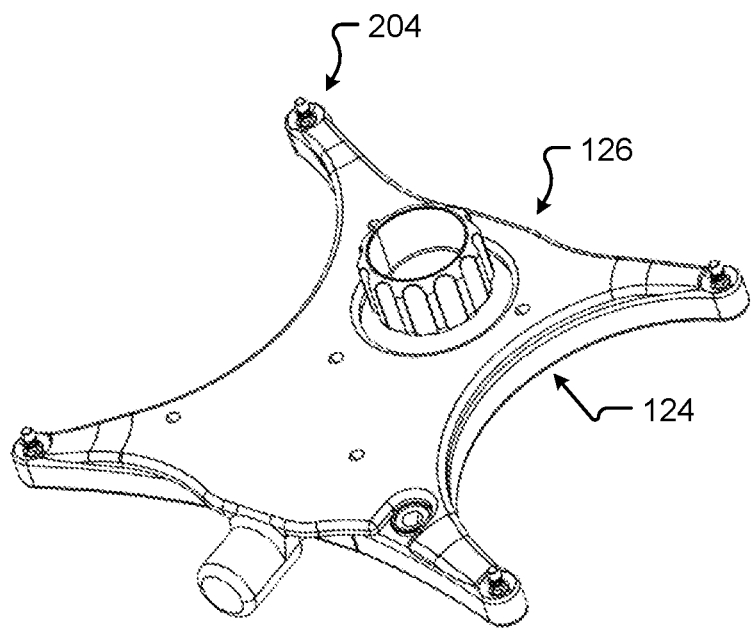
FIG. 4A is a tilted view of a reference frame adapter and a reference frame according to at least one embodiment of the present disclosure.
Figure 4B:
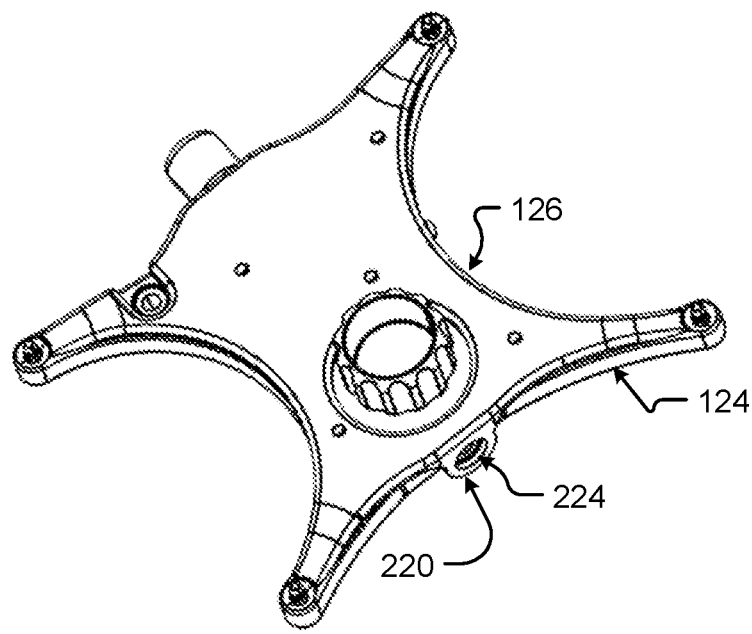
FIG. 4B is a tilted view of the reference frame adapter and the reference frame of FIG. 4A according to at least one embodiment of the present disclosure.
Figure 4C:
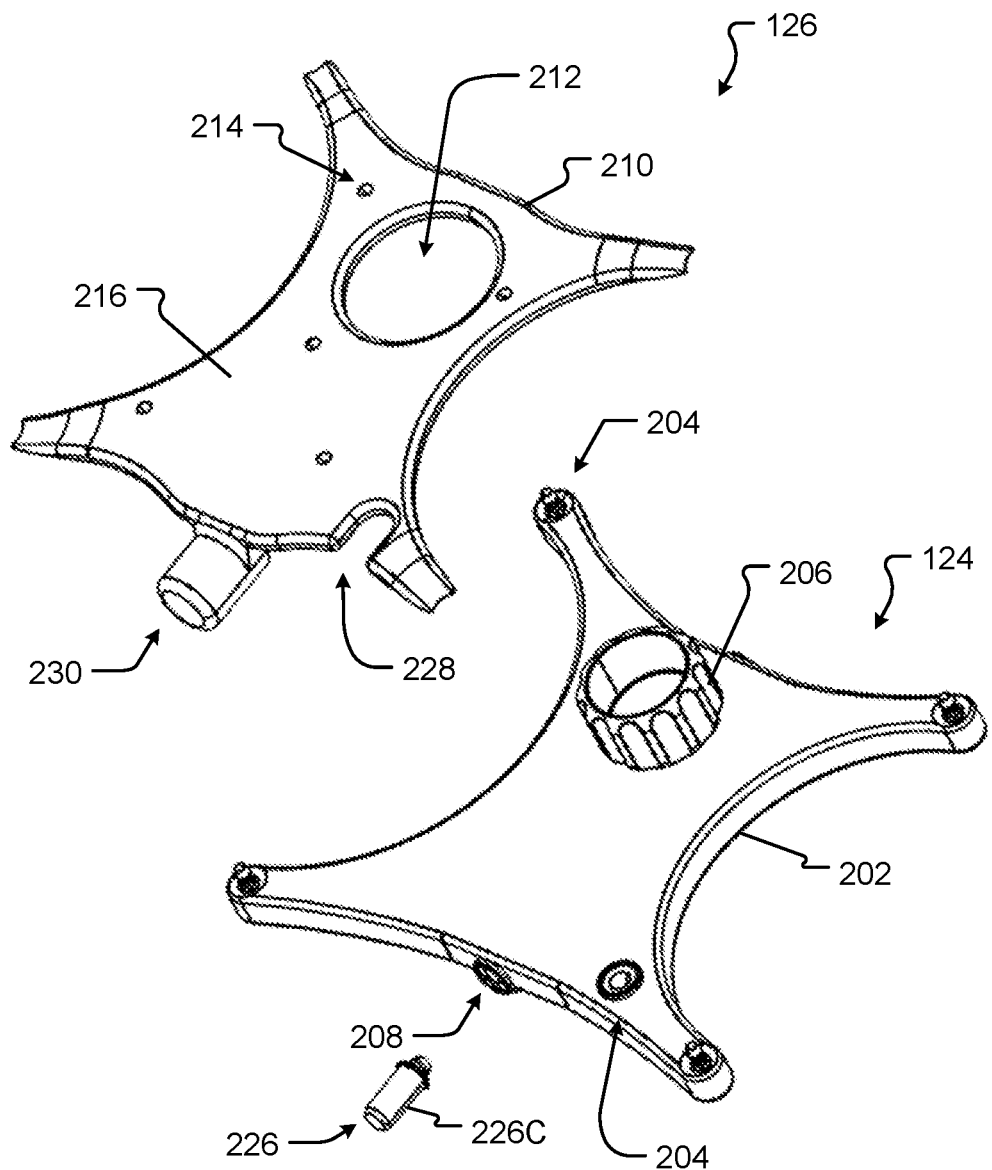
FIG. 4C is an exploded view of the reference frame adapter and the reference frame of FIG. 4A according to at least one embodiment of the present disclosure.

Turning to FIGS. 4A-4C, a tilted view, another tilted view, and an exploded view of the reference frame 124 and another embodiment of the reference frame adapter 126 according to at least one embodiment of the present disclosure are respectively shown. The reference frame adapter 126 is the same as or similar to the reference frame adapter 126, except that the body 210 includes a slot 208 to expose another receiver 204 on the reference frame 124. In some instances, the body 210 may comprise an aperture or any shaped opening instead of the slot 208. In still other instances, the body 210 may not include the slot 208. The reference frame adapter 126 in the illustrated embodiment also comprises a pin 226C which may be similar to the pin 226A as described in FIGS. 2A-2C. The pin 226C is also movable between a closed position and an open position and is also biased (whether by a spring or otherwise) in the closed position. The pin 226C is received in a housing 230 integrated into the first side wall 218. The pin 226C is positioned closer towards the second side wall 220 when in the closed position and further away from the second side wall 220 when in the open position. Thus, when the reference frame adapter 126 is positioned over the reference frame 124 and the pin 226C is aligned with the reference frame aperture 208, the pin 226C is biased to the closed position and into the reference frame aperture 208, thereby securing the reference frame adapter 126 to the reference frame 124. To remove the reference frame adapter 126, the pin 226C is moved to the open position by receiving a force (from, for example, a user) to pinch the pin 226C through the housing 230 and to pull the pin 226C away from the first side wall 218 and into the open position such that the pin 226C is not received by the reference frame aperture 208 and the reference frame adapter 126 can be removed from the reference frame 124.

Figure 5:
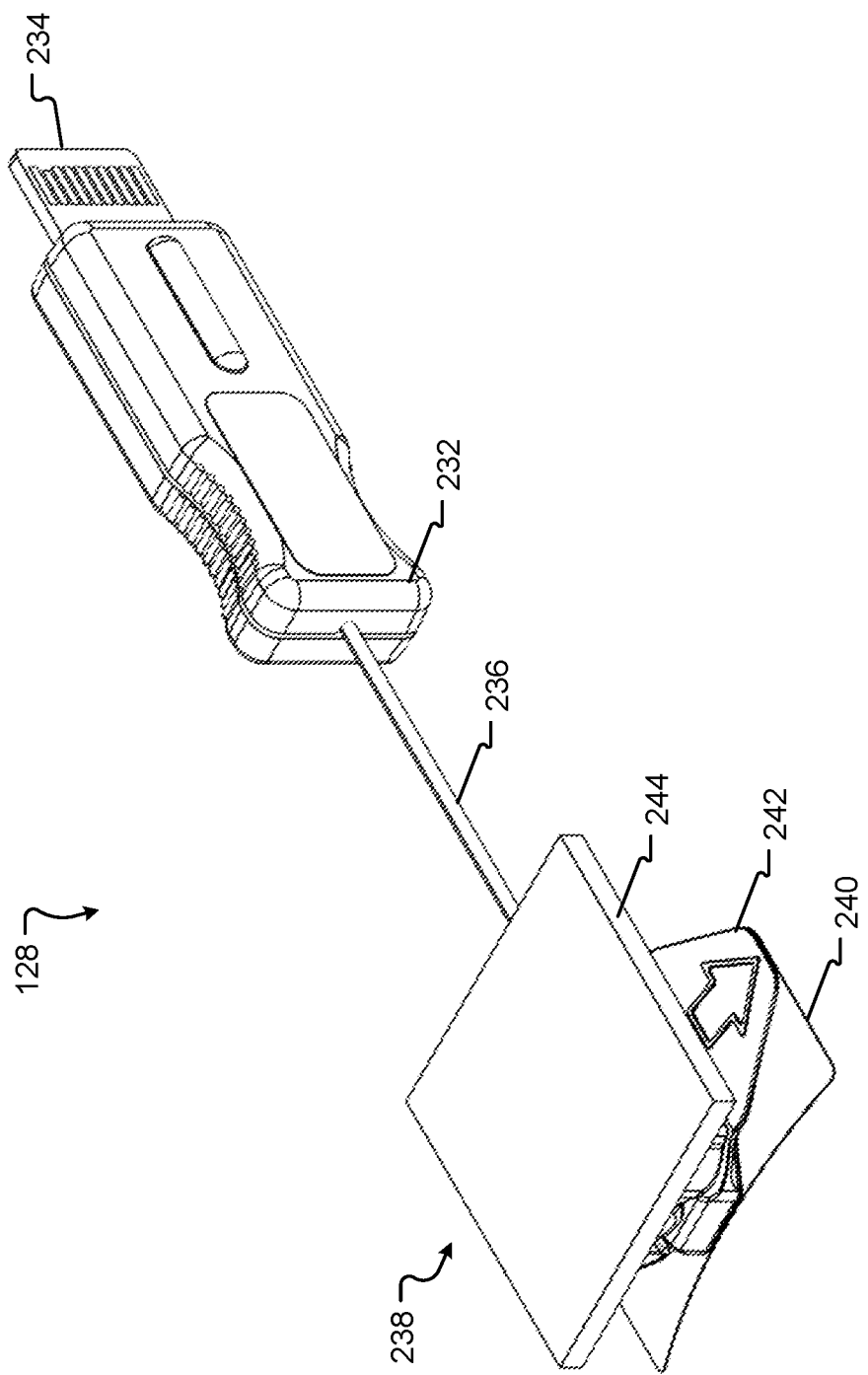
FIG. 5 is an isometric view of an electromagnetic (EM) reference frame adapter according to at least one embodiment of the present disclosure.

Turning to FIG. 5, an isometric view of an EM reference frame adapter 128 according to at least one embodiment of the present disclosure is shown. The EM reference frame adapter 128 comprises a base 232 having a stem 236 extending from an end of the base 232 and a plug 234 extending from an opposite end. The plug 234 is configured to be received by the EM tracker 132. The stem 236 connects to a reference frame body 238 comprising a backing 240, a directional portion 242, and a reference frame 244 that is easily detectable by, for example, an imaging device comprising a 3D scanner. Thus, during, for example, a registration process that uses a 3D scanner, the 3D scanner can detect a pose of the EM reference frame adapter 128 and the detected pose of the EM reference frame adapter 128 can be used to register the EM tracker 132. When the registration process is completed, the reference frame adapter 126 may be removed from the EM tracker 132 and the navigation system 118 may track the EM tracker 132. It will be appreciated that the reference frame body 238 may comprise any combination of components or may comprise more or less components than described.

It will be appreciated that the reference frame adapter 126 and the EM reference frame adapter 128 described above are examples reference frame adapters. Thus, the reference frame adapter 126 and/or the EM reference frame adapter 128 may include any combination of features described above. For example, the reference frame adapter 126 may include the slot 208 and the pin 226 and the reference frame aperture 208 may be threaded. In another example, the reference frame adapter 126 may not include the pin 226 and the reference frame adapter 126 may be releasably secured to the reference frame 124 by a snap fit. It will also be appreciated that the reference frame adapter 126 may be any shape or size and can be shaped to fit over any reference frame 124. Further, the reference frame adapter 126 may also include any feature or component not described herein.

Figure 6:
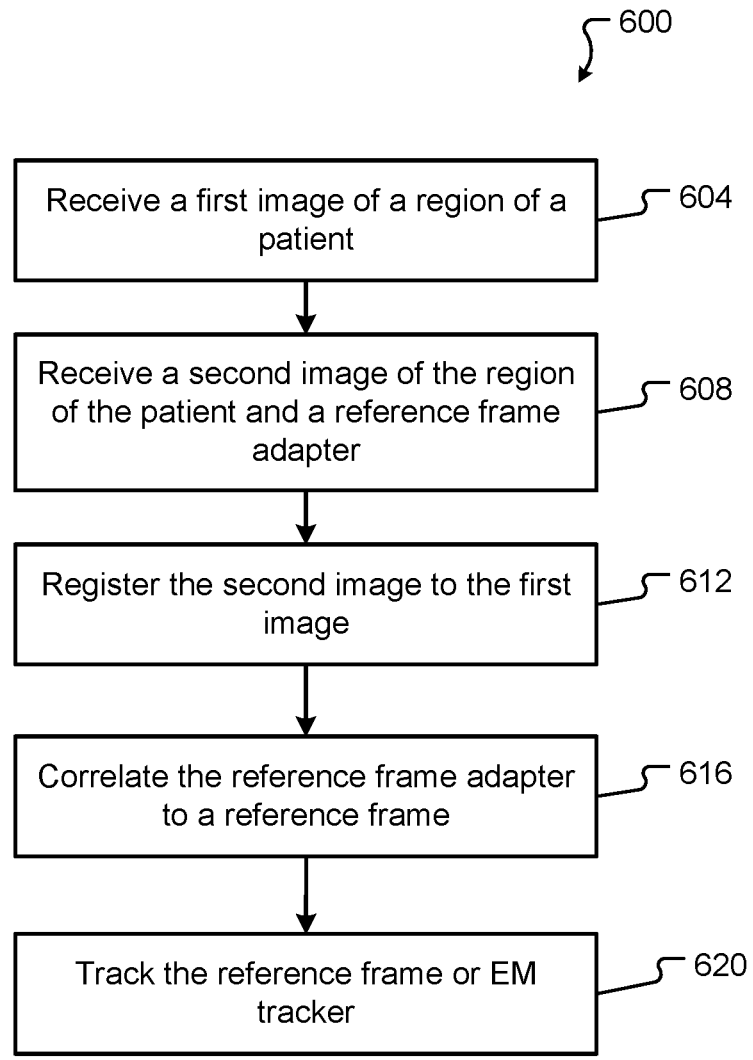
FIG. 6 is a flowchart according to at least one embodiment of the present disclosure.

FIG. 6 depicts a method 600 that may be used, for example, for contactless registration using a reference frame adapter such as the reference frame adapter 126 or the EM reference frame adapter 128.

The method 600 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 600. The at least one processor may perform the method 600 by executing elements stored in a memory such as the memory 106. The elements stored in memory and executed by the processor may cause the processor to execute one or more steps of a function as shown in method 600. One or more portions of a method 600 may be performed by the processor executing any of the contents of memory, such as an image processing 120 and/or a registration 122.

The method 600 comprises receiving a first image of a region of a patient (step 604). One or more first images may be received in the step 604. The first image may be received via a user interface such as the user interface 110 and/or a communication interface such as the communication interface 108 of a computing device such as the computing device 102, and may be stored in a memory such as the memory 106 of the computing device. The first image may also be received from an external database or image repository (e.g., a hospital image storage system, such as a picture archiving and communication system (PACS), a health information system (HIS), and/or another system for collecting, storing, managing, and/or transmitting electronic medical records including image data), and/or via the Internet or another network. In other embodiments, the first image may be received or obtained from an imaging device such as the imaging device 112, which may be any imaging device such as an MRI scanner, a CT scanner, any other X-ray based imaging device, or an ultrasound imaging device. The first image may also be generated by and/or uploaded to any other component of a system such as the system 100. In some embodiments, the first image may be indirectly received via any other component of the system or a node of a network to which the system is connected.

The first image may be a 2D image or a 3D image or a set of 2D and/or 3D images. The first image may depict a patient's anatomy or portion thereof. In some embodiments, the first image may be captured preoperatively (e.g., before surgery) and may be stored in a system (e.g., a system 100) and/or one or more components thereof (e.g., a database 130). The stored image may then be received (e.g., by a processor 104), as described above, preoperatively (e.g., before the surgery) and/or intraoperatively (e.g., during surgery). In some embodiments, the first image may depict multiple anatomical elements associated with the patient anatomy, including incidental anatomical elements (e.g., ribs or other anatomical objects on which a surgery or surgical procedure will not be performed) in addition to target anatomical elements (e.g., vertebrae or other anatomical objects on which a surgery or surgical procedure is to be performed). The first image may comprise various features corresponding to the patient's anatomy and/or anatomical elements (and/or portions thereof), including gradients corresponding to boundaries and/or contours of the various depicted anatomical elements, varying levels of intensity corresponding to varying surface textures of the various depicted anatomical elements, combinations thereof, and/or the like. The first image may depict any portion or part of patient anatomy and may include, but is in no way limited to, one or more vertebrae, ribs, lungs, soft tissues (e.g., skin, tendons, muscle fiber, etc.), a patella, a clavicle, a scapula, combinations thereof, and/or the like.

Each first image may be processed by a processor such as the processor 104 using an image processing algorithm such as the image processing algorithm 120 to identify anatomical elements and/or objects (such as, for example, a reference frame adapter 126, an EM reference frame adapter 128, and/or one or more reference markers disposed on a reference frame 124, the reference frame adapter 126, and/or the EM reference frame adapter 128) in the image. In some embodiments, feature recognition may be used to identify a feature of the anatomical element or the object(s). For example, a contour of a vertebrae, femur, or other bone may be identified in the image. In other embodiments, the image processing algorithm may use artificial intelligence or machine learning to identify the anatomical element and/or the object(s).

The method 600 also comprises receiving a second image of the region of the patient and a reference frame adapter (step 608). The step 608 may be the same as or similar to the step 604 with respect to receiving and processing the second image. The second image may be received after the first image. In some embodiments, the second image may comprise a 3D scan which may be received from, for example, an imaging device comprising a 3D scanner.

The second image may also depict the reference frame adapter which may be the same as or similar to the reference frame adapter 126 or the EM reference frame adapter 128. As described in detail in FIGS. 2A-5, the reference frame adapter or the EM reference frame adapter may be visible or detectable when the imagining device comprises a 3D scanner. The 3D scanner may have difficulty detecting a conventional reference frame or EM tracker. Thus, the reference frame adapter or the EM reference frame adapter can be attached to the reference frame or the EM tracker when the 3D scanner is used to obtain the second image and can be removed from the reference frame or the EM tracker when the 3D scanner is not in use. For example, the reference frame may be a patient reference frame and the region of the patient may be a head of the patient. The patient reference frame may be positioned near the patient's head. During an initial registration, a 3D scanner may be used to perform a touchless registration. Because the patient reference frame may be difficult to detect by the 3D scanner, the patient reference frame adapter may be attached to the patient reference frame during the initial registration. Once the initial registration is completed, the patient reference frame adapter may be removed from the patient reference frame. The patient reference frame can then be tracked by a navigation system such as the navigation system 118.

The method 600 also comprises registering the second image to the first image (step 612). The step 224 may make use of a processor (e.g., a processor 104) utilizing a registration algorithm, such as a registration algorithm 122. The registration algorithm may transform, map, or create a correlation between the second image and/or components thereof and the first image, which may then be used by a system (e.g., a system 100) and/or one or more components thereof (e.g., the navigation system) to translate one or more coordinates in the patient coordinate space to one or more coordinates in a coordinate space of the navigation system and/or a coordinate space of a robot such as the robot 114 and/or vice versa. As previously noted, the registration may comprise registering between second image and the first image and/or vice versa.

In some embodiments, the registration may be based on one or more gradients. For example, the registration algorithm may align, match, and/or map one or more gradients from the second image to a corresponding one or more gradients in the first image. In some embodiments, the registration algorithm may determine a first set of identifiers or characteristics associated with the one or more gradients depicted in the second image (e.g., pixel values, changes in one or more pixel values in a variety of directions, average pixel value change in one or more directions in the image, etc.) and compare the identifiers or characteristics to a second set of identifiers or characteristics calculated based the first image. Based on similarities or patterns between the two sets of identifiers or characteristics (e.g., same pixel value changes), the registration algorithm may determine that a gradient present in the second image corresponds to a gradient present in the first image. The determined presence of the corresponding gradients in both images may allow the processor to transform or map the location of one or more anatomical features in the second image to respective one or more anatomical features in the first image, or vice versa. Once completed, the registration is useful, for example, to facilitate a surgery or surgical task (e.g., controlling a robot and/or robotic arm with patient anatomy and/or providing image-based guidance to a surgeon).

In some embodiments, the registration may be performed one or more times intraoperatively (e.g., during surgery) to update, adjust, and/or refresh the current registration. For example, a new second image may be captured intraoperatively, and a new registration may be completed therefrom.

The method 600 also comprises correlating the reference frame adapter to the reference frame (step 616). The processor may correlate the detected pose of the reference frame adapter to a pose of reference frame. In some embodiments, a distance between the reference frame adapter and the reference frame (whether between first surfaces, center points, etc.) may be determined and the detected pose may be offset by the distance to yield a pose of the reference frame. In other embodiments, the detected pose may be offset by a thickness of the reference frame adapter. Similarly, a distance between the EM reference frame adapter and the EM tracker may be used to offset the detected pose to yield a pose of the EM tracker.

The method 600 also comprises tracking the reference frame or EM tracker (step 620). During the tracking, the reference frame adapter or the EM reference frame adapter may be removed from the reference frame or the EM tracker, respectively, after the step 616. Tracking the reference frame may include using the navigation system to track one or more markers of the reference frame or the track the EM tracker. As previously described, the reference frame may include a frame and the one or more reference markers may be disposed on the reference frame. As previously described, the reference frame adapter or the EM reference frame adapter enable the use of conventional reference frames or EM trackers throughout an entire surgical procedure without changing components or having to use a new reference frame. Thus, the reference frame adapter or the EM reference frame adapter can be attached to the reference frame or the EM transmitter during, for example, an initial registration of a surgical procedure. The reference frame adapter or the EM reference frame adapter can be removed from the reference frame or the EM tracker, respectively, and the reference frame or the EM tracker can be tracked throughout a remaining portion of the surgical procedure by the navigation system.

It will be appreciated that the method 600 and any steps therein may be repeated during a surgical procedure. For example, as previously described, a new registration may be performed and, in such instances, the steps 608-620 may be repeated. The method 600 and/or any steps therein may be repeated multiple times.

The present disclosure encompasses embodiments of the method 600 that comprise more or fewer steps than those described above, and/or one or more steps that are different than the steps described above.

As noted above, the present disclosure encompasses methods with fewer than all of the steps identified in FIG. 6 (and the corresponding description of the method 600), as well as methods that include additional steps beyond those identified in FIG. 6 (and the corresponding description of the method 600). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for contactless registration comprising:
a processor;
a patient reference frame;
a reference frame adapter configured to selectively attach to the patient reference frame, wherein the reference frame adapter includes at least one aperture configured to receive a pin configured to pass through the at least one aperture and is received by a second aperture in the patient reference frame; and
a memory storing data for processing by the processor, the data, when processed, causes the processor to:
receive a first image of a region of a patient;
receive a second image of the region of the patient, wherein the second image includes the patient reference frame and the reference frame adapter, positioned near the region of the patient;
use an image processing algorithm to register the second image to the first image based on the reference frame adapter, wherein the image processing algorithm comprises a machine learning model trained using image data, and wherein registering the second image to the first image comprises determining information about an anatomical element and/or the patient reference frame in the first image and the second image; and
perform a surgical task based on the determined information about the anatomical element and/or the patient reference frame.

2. The system of claim 1, wherein the reference frame adapter includes at least one reference marker disposed on a surface of the reference frame adapter.

3. The system of claim 1, wherein the patient reference frame includes at least one reference marker disposed on a surface of the patient reference frame.

4. The system of claim 1, wherein the at least one aperture included in reference frame adapter is threaded, and wherein the pin is threaded.

5. The system of claim 1, wherein the reference frame adapter covers at least a portion of the patient reference frame.

6. The system of claim 1, wherein the second image comprises a 3D scan and the region of the patient comprises a face of the patient.

7. The system of claim 1, further comprising a navigation system configured to track the patient reference frame, wherein the memory stores further data for processing by the processor that, when processed, causes the processor to:
correlate a pose of the reference frame adapter with a pose of the patient reference frame; and
track the patient reference frame.

8. The system of claim 7, wherein the reference frame adapter is removed from the patient reference frame after the second image is registered to the first image.

9. A system for contactless registration comprising:
a processor;
a patient electromagnetic (EM) tracker;
an EM reference frame adapter configured to selectively attach to the patient EM tracker, wherein the EM reference frame adapter includes at least one aperture configured to receive a pin configured to pass through the at least one aperture and is received by a second aperture in the patient EM tracker; and
a memory storing data for processing by the processor, the data, when processed, causes the processor to:
receive a first image of a region of a patient;
receive a second image of the region of the patient and the patient EM tracker positioned near the region of the patient; and
use an image processing algorithm to register the second image to the first image based on the EM reference frame adapter, wherein the image processing algorithm comprises a machine learning model trained using image data, and wherein registering the second image to the first image comprises determining information about an anatomical element and/or the patient EM tracker in the first image and the second image; and
perform a surgical task based on the determined information about the anatomical element and/or the patient EM tracker.

10. The system of claim 9, wherein the EM reference frame adapter includes at least one reference marker disposed on a surface of the EM reference frame adapter.

11. The system of claim 9, wherein the at least one aperture in the EM reference frame adapter is threaded.

12. The system of claim 9, wherein the second image comprises a 3D scan and the region of the patient comprises a face of the patient.

13. The system of claim 9, further comprising a navigation system configured to track the patient EM tracker, wherein the memory stores further data for processing by the processor that, when processed, causes the processor to:
correlate a pose of the EM reference frame adapter with a pose of the patient EM tracker; and
track the patient EM tracker.

14. The system of claim 9, wherein the EM reference frame adapter is removed from the patient EM tracker after the second image is registered to the first image.

15. A system for contactless registration comprising:
a navigation system configured to track a patient reference frame, wherein the patient reference frame includes a reference frame adapter configured to selectively attach to the patient reference frame, wherein the reference frame adapter includes at least one aperture configured to receive a pin configured to pass through the at least one aperture and is received by a second aperture in the patient reference frame;
a processor; and
a memory storing data for processing by the processor, the data, when processed, causes the processor to:
receive a first image of a region of a patient;
receive a second image of the region of the patient and the reference frame adapter and the patient reference frame positioned near the region of the patient;
use an image processing algorithm to register the second image to the first image based on the reference frame adapter, wherein the image processing algorithm comprises a machine learning model trained using image data, and wherein registering the second image to the first image comprises determining information about an anatomical element and/or the patient reference frame in the first image and the second image; and
cause the navigation system to track the patient reference frame.

16. The system of claim 15, wherein the reference frame adapter includes at least one reference marker disposed on a surface of the reference frame adapter.

17. The system of claim 15, wherein the patient reference frame includes at least one reference marker disposed on a surface of the patient reference frame.

18. The system of claim 15, wherein the at least one aperture in the reference frame adapter is threaded and the pin is threaded.

19. The system of claim 15, wherein the reference frame adapter covers at least a portion of the patient reference frame.

20. The system of claim 15, wherein the memory stores further data for processing by the processor that, when processed, causes the processor to:
correlate a pose of the reference frame adapter with a pose of the patient reference frame.

* * * * *